(12) United States Patent
West et al.

(10) Patent No.: US 8,915,955 B2
(45) Date of Patent: Dec. 23, 2014

(54) STENT GRAFT FIXATION COUPLING

(75) Inventors: Karl J. West, Geneva, OH (US); Roy K. Greenberg, Bratenahl, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1081 days.

(21) Appl. No.: 12/546,232

(22) Filed: Aug. 24, 2009

(65) Prior Publication Data

US 2010/0057186 A1 Mar. 4, 2010

Related U.S. Application Data

(60) Provisional application No. 61/092,150, filed on Aug. 27, 2008.

(51) Int. Cl.
| | |
|---|---|
| A61F 2/06 | (2013.01) |
| A61F 2/07 | (2013.01) |
| A61F 2/954 | (2013.01) |
| A61F 2/91 | (2013.01) |
| A61F 2/95 | (2013.01) |
| A61F 2/89 | (2013.01) |

(52) U.S. Cl.
CPC ........... *A61F 2/064* (2013.01); *A61F 2002/075* (2013.01); *A61F 2/07* (2013.01); *A61F 2/954* (2013.01); *A61F 2/91* (2013.01); *A61F 2/95* (2013.01); *A61F 2220/0075* (2013.01); *A61F 2/89* (2013.01); *A61F 2002/061* (2013.01)
USPC ........ 623/1.31; 623/1.13; 623/1.35; 623/1.16

(58) Field of Classification Search
None
See application file for complete search history.

(56) References Cited

U.S. PATENT DOCUMENTS

| | | | | |
|---|---|---|---|---|
| 6,524,322 | B1 * | 2/2003 | Berreklouw | 606/153 |
| 6,616,675 | B1 | 9/2003 | Evard et al. | 606/155 |
| 6,890,349 | B2 * | 5/2005 | McGuckin et al. | 623/1.13 |
| 2002/0082627 | A1 | 6/2002 | Berg et al. | 606/155 |
| 2004/0167551 | A1 * | 8/2004 | Gifford et al. | 606/153 |
| 2006/0155359 | A1 * | 7/2006 | Watson | 623/1.13 |
| 2008/0167704 | A1 | 7/2008 | Wright et al. | 623/1.12 |

OTHER PUBLICATIONS

"Ellipse", Math Open Reference, pp. 1-3, accessed Nov. 4, 2011.*
International Search Report and Written Opinion of the International Searching Authority for International Application No. PCT/US2009/004805, dated Oct. 14, 2009, 10 pages.

* cited by examiner

*Primary Examiner* — Thomas J Sweet
*Assistant Examiner* — Rebecca Preston
(74) *Attorney, Agent, or Firm* — Brinks Gilson & Lione

(57) ABSTRACT

A small vessel stent graft with a fixation coupling that has a hyperboloid shape positioned at or near the proximal end of the graft. The coupling may be deployed within the fenestration of a fenestrated graft to provide multi-directional movement without compromising the integrity of the sealing zone.

5 Claims, 6 Drawing Sheets

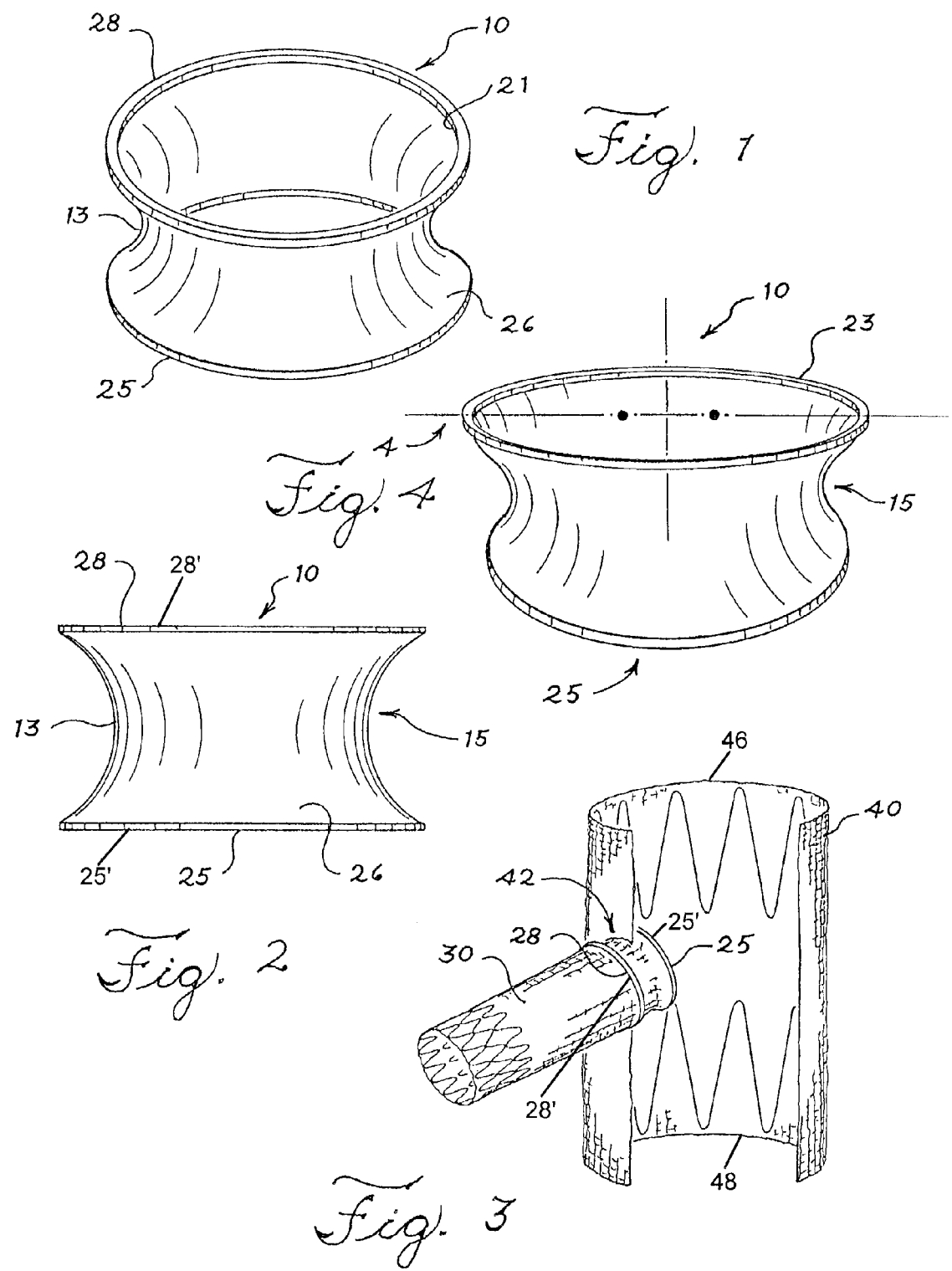

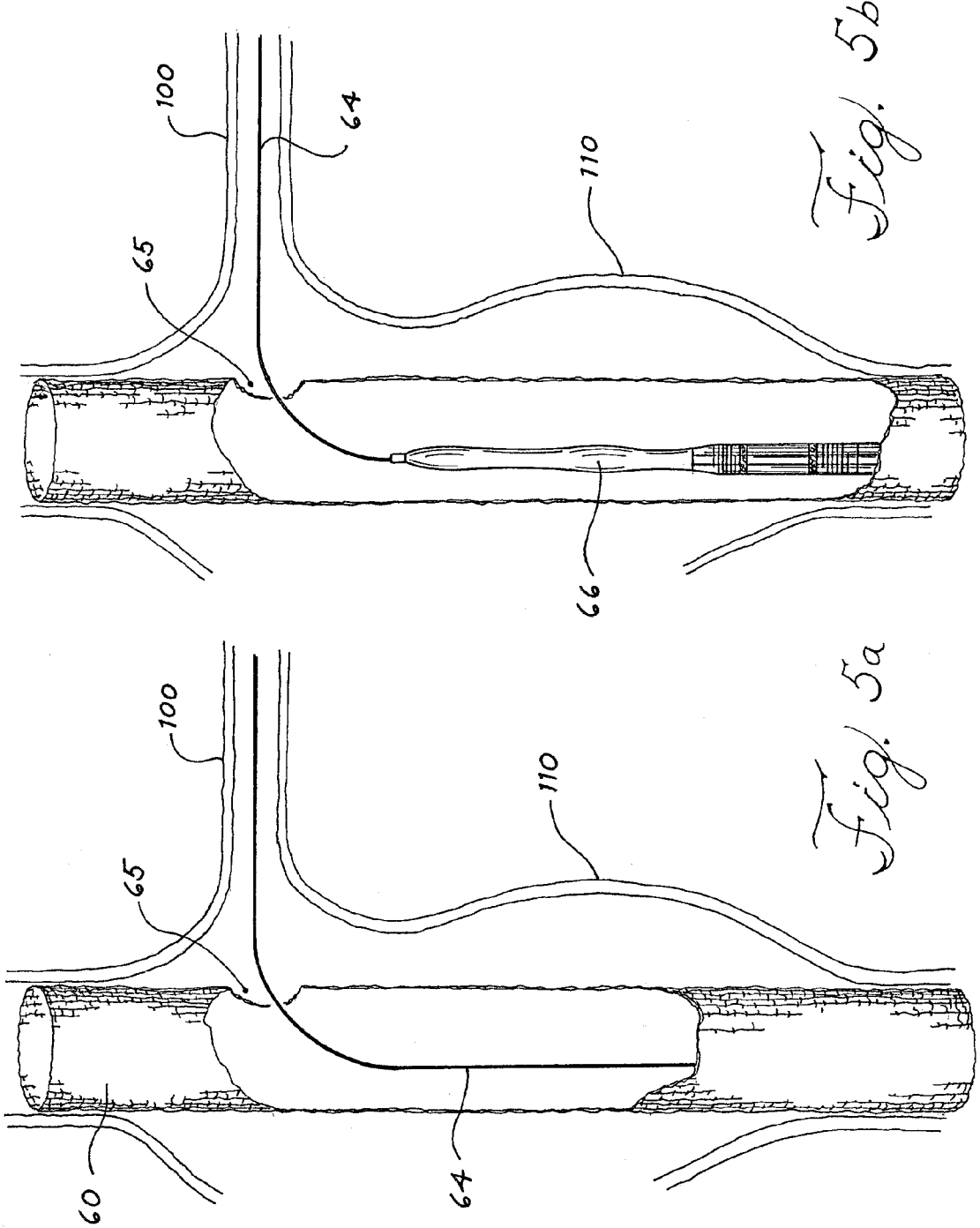

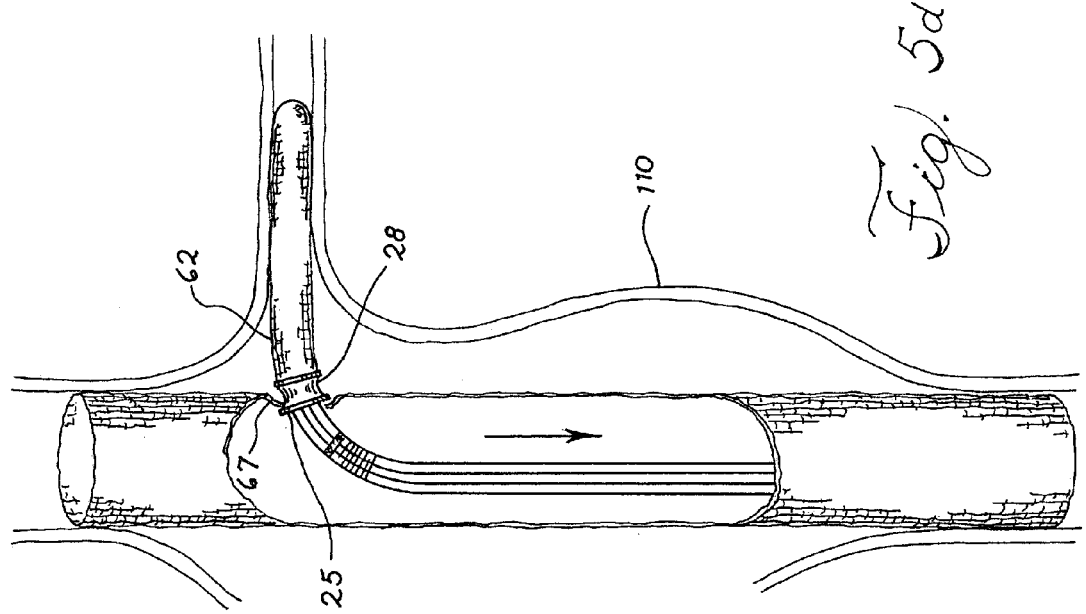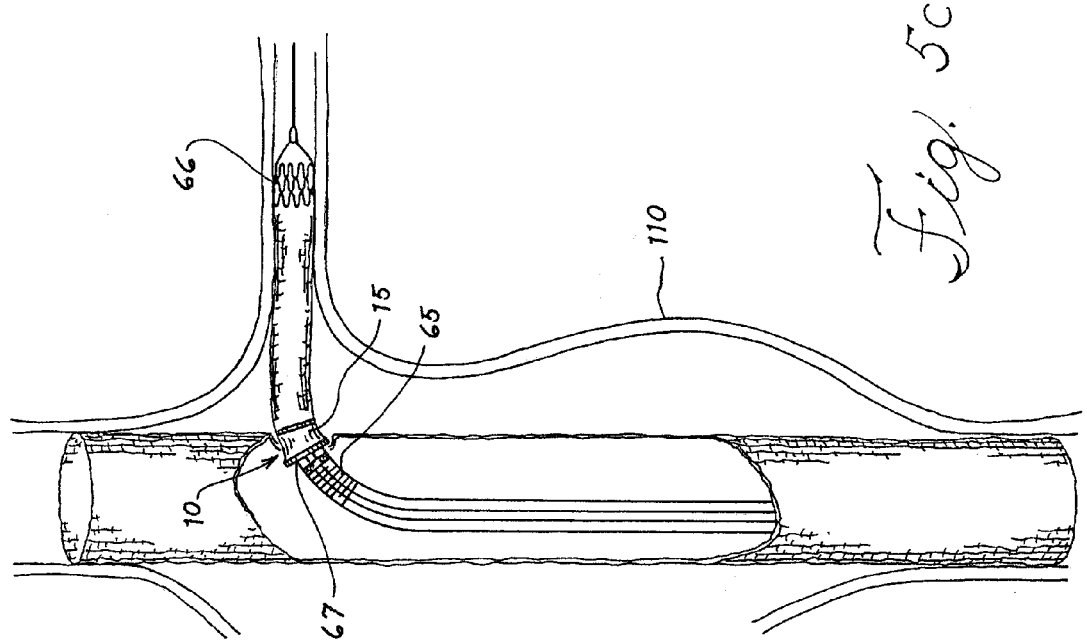

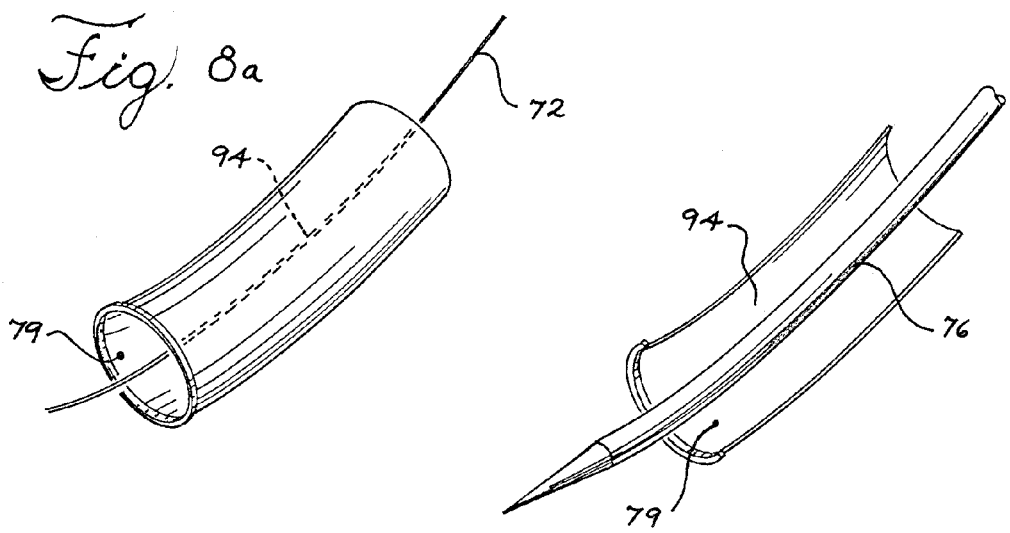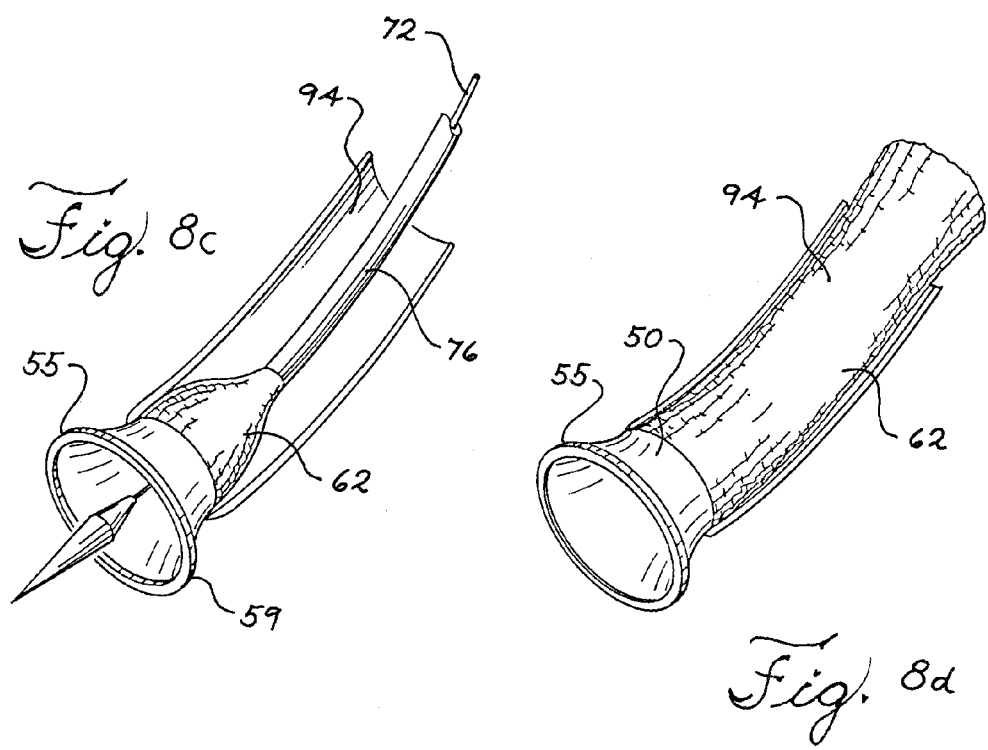

US 8,915,955 B2

STENT GRAFT FIXATION COUPLING

CROSS-REFERENCE TO RELATED APPLICATIONS

This application claims the benefit of U.S. Provisional Application No. 61/092,150, filed Aug. 27, 2008, which is incorporated by reference in its entirety.

TECHNICAL FIELD

The present invention relates to a fixation joint for use with a fenestrated stent graft and a smaller branch stent that provides secure and complete rotational movement. This invention also relates to methods for deploying the same.

BACKGROUND

Using stent grafts to treat aneurysms is common in the medical field. Stent grafts are deployed by accessing a vasculature with a small incision in the skin and guiding a delivery system to the target area. This intraluminal delivery is less invasive and generally preferred over more intrusive forms of surgery. Multiple stent grafts may be implanted using intraluminal delivery to provide a system of interconnected stent grafts. Interconnected stent grafts can be made of fenestrated grafts and smaller side branch stents, including bifurcated grafts.

Sometimes aneurysms engulf a vessel and its branch vessels, such as the aorta and the renal arteries or the aortic arch and the branch arteries. In such instances a fenestrated graft can be implanted in the main vessel while smaller branch grafts can be deployed in the branch arteries. The main vessel grafts have fenestrations that correspond with the opening of the branch vessel. The smaller branch grafts are joined with the main vessel graft at the fenestrations. Due to the torsion and rigors of the endovascular system, this juncture can be subject to significant stress.

BRIEF SUMMARY

An endoluminal prosthesis is provided that includes a proximal end, a distal end, a body portion configured for placement in a body vessel branching from a main body vessel, and a fixation coupling. The fixation coupling may be positioned at or near the proximal end of the prosthesis and configured for placement within the fenestration of a fenestrated device. The fixation coupling may include a distal non-helical ring, a proximal non-helical ring, and a hyperboloid area positioned between the rings. There may be first and second outer extents in the hyperboloid area. The diameter of at least one of the rings may be larger than any diameter of the hyperboloid area.

Also disclosed is a method of deploying a system of endoluminal prostheses with a fixation coupling that provides angular and rotating movement in a body having a primary vessel in communication with a secondary vessel. The system may include a first prosthesis for implantation in the primary vessel that includes a tubular wall, a lumen therethrough, and a fenestration in the tubular wall. The system may also include a second prosthesis for implantation in the secondary vessel. The second prosthesis may include a fixation coupling that has a distal non-helical ring, a proximal non-helical ring, and a hyperboloid area positioned between the rings. The hyperboloid area may have first and second outer extents. The diameter of at least one of the rings may be larger than any diameter of the hyperboloid area.

The method may include deploying the first prosthesis in the primary vessel and aligning the fenestration with the secondary vessel. The fixation coupling may be deployed in the fenestration by placing the proximal non-helical ring in the lumen of the first prosthesis and abutting the proximal ring against an internal portion of the wall surrounding the fenestration. The distal non-helical ring may be placed outside the lumen of the first prosthesis and deployed such that the fenestration surrounds the hyperboloid area to form a joint.

The fixation coupling may also have a partial hyperboloid shape or bell-shape. A branch vessel stent graft may include a distal end and a body portion configured for placement in a body vessel branching from a main body vessel. Also, there may be a proximal end configured for at least partial placement within an internal branch of a branched stent graft. A fixation coupling may be positioned at or near the proximal end of the stent graft, where the fixation coupling may have a flared proximal opening with a diameter larger than any diameter of the stent graft. Also, there may be a ring surrounding the flared proximal opening.

There is a system for repairing an anatomical vessel at the junction of a main anatomical vessel and branch anatomical vessel that comprises a primary stent graft configured for placement in the main anatomical vessel. The primary stent graft comprises a tubular graft material, at least one stent, and a fenestration with a diameter in a sidewall of the tubular graft material. The system also includes a branch vessel stent graft that has a proximal end, a distal end, a body portion configured for placement in a body vessel branching from a main body vessel, and a fixation coupling positioned at or near the proximal end and configured for placement within the fenestration. The fixation coupling comprises a distal non-helical ring, a proximal non-helical ring, and a hyperboloid area positioned between the rings, and first and second outer extents. The diameter of at least one of the rings is larger than any diameter of the hyperboloid area and the smallest diameter of the hyperboloid area is at least the diameter of the fenestration.

BRIEF DESCRIPTION OF THE DRAWINGS

FIG. 1 is a perspective view of a hyperboloid shaped fixation coupling.

FIG. 2 is a side view of the hyperboloid shaped fixation coupling.

FIG. 3 is a longitudinal cross-sectional view of a fenestrated stent graft coupled to a hyperboloid shaped fixation coupling on the proximal end of a small vessel stent graft.

FIG. 4 is a perspective view of a hyperboloid shaped fixation coupling with an elliptical ring on one end.

FIGS. 5A-5F are cross sectional schematic diagrams showing the steps of deploying a stent graft having a hyperboloid shaped coupling into a renal artery and mating with a fenestrated stent graft implanted in the aorta.

FIGS. 8A-8D are cross-sectional views of the deployment steps of a secondary graft with a bell-shaped fixation coupling with a fenestrated stent graft.

DETAILED DESCRIPTION OF THE DRAWINGS AND THE PRESENTLY PREFERRED EMBODIMENTS

Figure 5F:
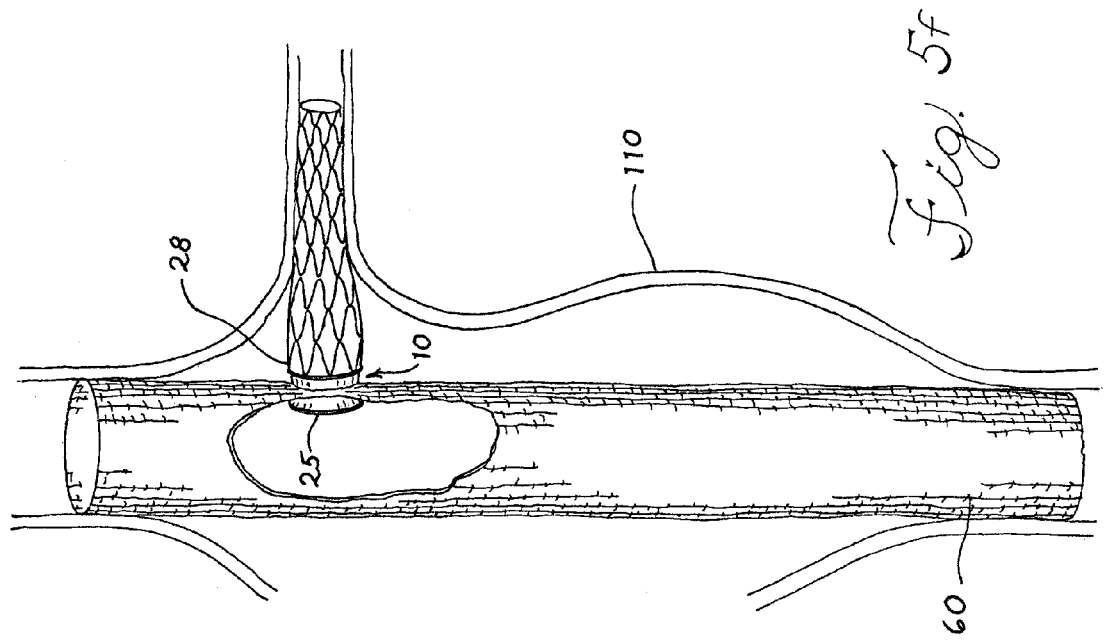

The term "prosthesis" means any replacement for a body part or for a function of that body part or any device that enhances or adds functionality to a physiological system.

The term "graft or graft material" means a generally cannular or tubular member which acts as an artificial vessel or prosthesis. A graft by itself or with the addition of other elements, such as structural components, may be an endoluminal prosthesis. The graft comprises a single material, a blend of materials, a weave, a laminate, or a composite of two or more materials.

The graft material is a biocompatible material that is both flexible and abrasion resistant. Furthermore, the graft material should be selected from those materials that are particularly well suited for thermoplastic deformation, such that the material may be thermoplastically fused to a stent. The woven graft material can be a woven polyester. The woven graft material may be a polyethylene terephthalate (PET), such as DACRON® (DUPONT, Wilmington, Del.) or TWILL-WEAVE MICREL® (VASCUTEK, Renfrewshire, Scotland). Woven polyesters, such as Dacron, possess varying degrees of porosity, where the degree of porosity may be selectively controlled based on the weaving or knitting process that is used to produce the woven polyester. Consequently, depending on the application, the porosity may be adjusted to encourage incorporation of a patient's tissue into the woven graft material, which in turn may more securely anchor the prosthesis within the patient's vessel or lumen. Furthermore, the degree of porosity may be adjusted also to provide a woven graft material that is impermeable to liquids, including blood or other physiological fluids.

Throughout this specification, when discussing the application of this invention to the aorta or other blood vessels, the term "distal," with respect to a prosthesis, is intended to refer to a location that is, or a portion of the prosthesis that when implanted is, further downstream with respect to blood flow. The term "distally" means in the direction of blood flow or further downstream. The term "proximal" is intended to refer to a location that is, or a portion of the prosthesis that when implanted is, further upstream with respect to blood flow. The term "proximally" means in the direction opposite to the direction of blood flow or further upstream.

A branch vessel stent graft may include a proximal end 46, a distal end 48, and a body portion configured for placement in a body vessel branching from a main body vessel. For instance, the branch vessel stent graft may be placed in a renal artery, which branches from the aorta, or in the innominate artery, which branches from the aortic arch. The stent graft also includes a fixation coupling positioned at or near the proximal end and configured for placement within a fenestration of a fenestrated device. The fenestrated device may be a fenestrated stent graft that may be placed in a main blood vessel. The fixation coupling may include a distal ring, a proximal ring, and a hyperboloid shaped region or area positioned between the rings. The rings may be non-helical. The fixation coupling also may have first and second outer extents that are hyperboloid areas closest to the proximal and distal rings. The diameter of at least one of the rings is greater than any diameter of the hyperboloid shaped region.

The hyperboloid fixation coupling 10 may include nitinol rings 25 and 28 on its proximal 25' and distal 28' ends that are self-expanding. The coupling 10 may be integrated with a small-vessel stent graft for joining with a fenestrated stent graft. FIG. 1 shows a fixation coupling 10 with two rings 25 and 28 that are placed on either side of the hyperboloid shaped region or area 15. The rings 25 and 28 may include radiopaque elements to assist an operator in viewing the placement under fluoroscopy. The hyperboloid shaped region 15 has an apex 13, or middle point, that is slightly larger in diameter than the diameter of the fenestration of a fenestrated graft 40 when not implanted. As shown in FIG. 3, when the coupling 10 is implanted, the apex 13 is squeezed to fit within the fenestration 42 and to provide a secure seal. The smallest diameter of the hyperboloid can be at least the diameter of the fenestration 42, and preferably larger than the diameter of the fenestration. The fenestration may be provided with a support ring surrounding the perimeter of the fenestration 42. The support ring may be made of a material that permits visualization of the support ring during deployment of the hyperboloid area 15 within the fenestration 42. The support ring also may be of a material that expands to a larger diameter and then contracts to a smaller diameter to contact and seal against the hyperboloid shaped region.

The fixation coupling 10 has two outer extents that are the outer most points on the material. The first 21 and second 26 outer extents are immediately adjacent to the distal 28 and proximal 25 rings, respectively. The outer extents have diameters that may be up to 20% larger in diameter than the apex 13. There may be couplings 10 with outer extents greater than 20% of the apex 13 diameter. When deployed, the distal 28 and proximal 25 rings expand the hyperboloid area 15 about the fenestration 42. Deployment seals off the fenestration 42 and connects the small vessel device 30 to the fenestrated stent graft 40 as shown in FIG. 3. The diameters of both rings 28 and 25 may be larger than any diameter in the hyperboloid area 15. The hyperboloid area 15 of the small vessel stent graft 30 allows for multi-directional movement without compromising the integrity of the sealing zone and, thus, reduces any stress on the small vessel stent graft 30. The hyperboloid area 15 may act also as a moveable joint resembling an open-ended ball joint.

FIG. 4 shows a fixation coupling 10 with a distal ring 23 that is elliptical. The bottom, or proximal, ring 25 is circular. Both rings in some fixation couplings 10 described herein may also be elliptical rings. The elliptical distal ring 23 has a directrix 4 that may be greater than any diameter in the hyperboloid area 15. The directrix 4 may also be greater than the fenestration diameter in the stent graft to which it may be attached. There can also be fenestrated grafts that include an elliptical fenestration.

There is a method of deploying a system of endoluminal prostheses with a fixation coupling that provides angular and rotational movement in a body having a primary vessel in communication with a secondary vessel. The system may include a first prosthesis for implantation in the primary vessel with the first prosthesis having a tubular wall, a lumen therethrough, and a fenestration in the tubular wall. The system may include also a second prosthesis for implantation in the secondary vessel. This second prosthesis may include a fixation coupling as described herein, where the diameter of at least one of the rings is larger than any diameter of the hyperboloid area.

The deployment methods provide accurate placement of the small vessel stent graft with fenestrated stent grafts. Tactile feedback is provided to the operator when one of the rings abuts the wall around the fenestration. A fully deployed ring will not go through the fenestration and, as such, the operator will feel such resistance. This will help prevent misplacing the coupling and the small vessel stent graft. This lets the surgeon know that the small vessel stent graft is properly placed before complete deployment.

The method may include deploying the first prosthesis 60 in a primary vessel and aligning the fenestration with a secondary vessel. The fixation coupling 10 may be deployed in the fenestration by placing the proximal ring 25 in the lumen of the first prosthesis 60 and abutting the proximal ring 25 against an internal side of the wall 67 surrounding the fenestration 65. The distal ring 28 may be placed outside the lumen of the first prosthesis 60 and deployed such that the fenestration 65 surrounds the hyperboloid area 15 to form a joint.

As shown in FIG. 5A, the first prosthesis is a fenestrated graft 60 that has been implanted into a primary vessel, such as an aorta, having an aneurysm 110. The fenestration 65 is aligned with the opening of the branch vessel, such as the renal artery 100. Radiopaque markers may be used in placing the fenestrated graft 60 in the artery. A guidewire 64 is threaded through the fenestrated graft 60, through the fenestration 65, and into the renal artery. A balloon expandable or self-expanding small vessel stent graft 62 with a fixation coupling is inserted over the guidewire 64 in FIG. 5B using a delivery system 66. The delivery system 66 is advanced through the fenestration 65 and into the renal artery 100.

Figure 5E:
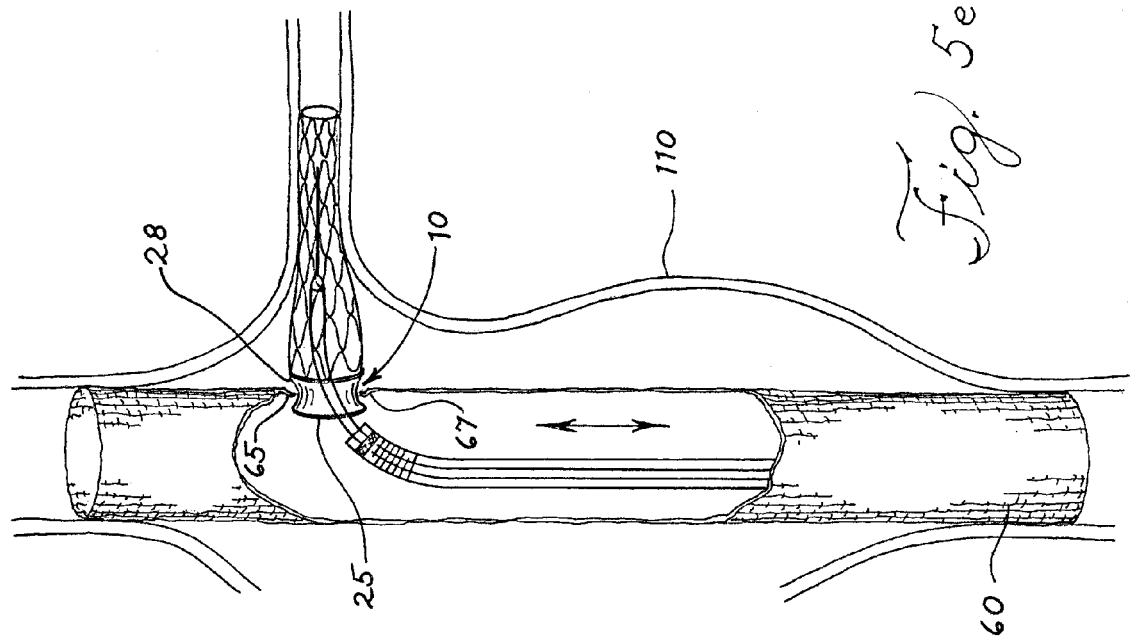

In FIG. 5C, the delivery system 66 has been advanced until the proximal ring 25 of the fixation coupling 10 is proximal to the internal side of the wall 67 surrounding the fenestration 65 and the distal ring 28 is on the distal side of the fenestration 65. The hyperboloid section 15 is surrounded by the fenestration 65. In FIG. 5D, the proximal ring 25 has been deployed while the distal ring 28 is only partially deployed. When the proximal ring 25 is pushed in a distal direction to abut the wall 67 surrounding the fenestration 65, the distal second ring 28 may be deployed fully as shown in FIG. 5E. FIG. 5F shows the system of endoprostheses with a fixation coupling 10 when implantation is complete.

The method also may include a step where the small vessel stent graft 62 is advanced into a branch vessel such as the renal artery 100 until the distal ring 28 is just distal to the fenestration 65 and deployed. The small vessel stent graft 62 may be pulled in a proximal direction such that the deployed distal ring 28 abuts the external side of the wall surrounding the fenestration 65. The proximal ring 25 may then be deployed to surround the fenestration 65 with the fixation coupling 10. In another method, the proximal ring 25 can be deployed while advancing the small vessel stent graft 62 through the fenestrated graft 60. Once the proximal ring 25 abuts the wall 67 surrounding the fenestration 65, the operator can feel the obstruction. The deployed proximal ring 25 provides tactile feedback when abutting the wall 67.

A branch vessel stent graft may include a distal end and a body portion configured for placement in a body vessel branching from a main body vessel. There may be a proximal end configured for at least partial placement within an internal branch of a branched stent graft. The small vessel stent graft 62 also may have a fixation coupling 50 positioned at or near the proximal end, where the fixation coupling 50 includes a flared proximal opening 57 with a diameter larger than any diameter of the small vessel stent graft 62, and a ring 55 surrounding the flared proximal opening 57.

Figure 6:
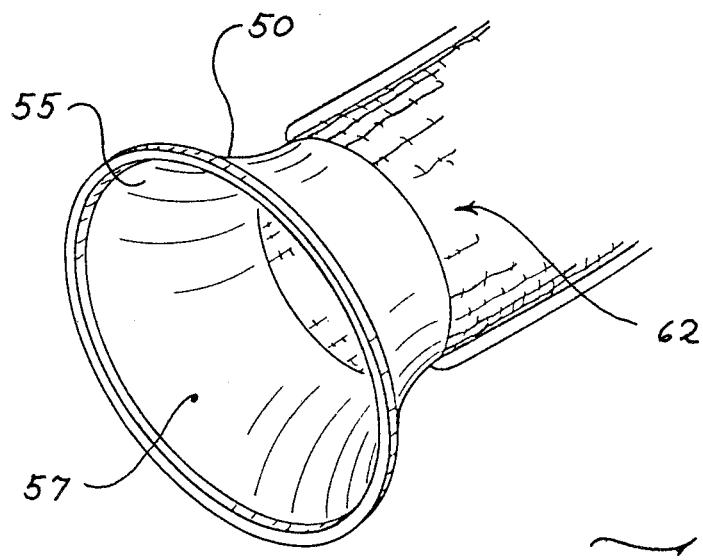
FIG. 6 is a perspective view of a bell shaped fixation coupling in an internal branch.

FIG. 6 shows a bell-bottomed shape fixation coupling 50. This fixation coupling 50 may be integrated with the proximal portion of the small vessel stent graft 62. A ring 55 is at the flared proximal opening 57 and may be stitched around the opening 57 or embedded in the graft material. The fixation coupling 50 may be self-expanding or balloon expandable. The ring 55 may include radiopaque elements and have an elliptical shape. If the ring 55 is an ellipse, the flared proximal opening 57 may be an ellipse also. The directrix of an elliptical ring and the flared proximal elliptical opening may be larger than any diameter in the bell-bottomed fixation coupling 50.

Figure 7:
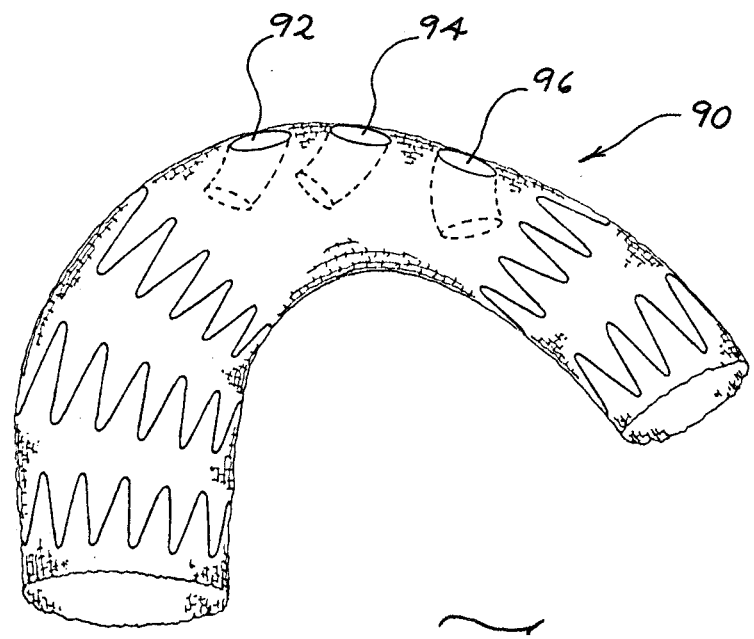
FIG. 7 is an internally branched stent graft for implantation in the aortic arch.

The bell-bottomed shaped fixation coupling 50 may be implanted in the internal branches 92, 94, 96 of an arch branch device 90 as shown in FIG. 7. The internal branches 92, 94, 96 correspond, respectively, to the innominate, left common carotid, and the left subclavian arteries when the device 90 is planted in the aortic arch. FIGS. 8A-8D show steps that may be used in deploying a small vessel stent graft 62 with a bell-bottomed fixation coupling 50 into internal branch 94. A guidewire 72 is inserted through a small incision made in the patient's neck to access the left common carotid artery. The guidewire 72 is advanced through the artery and then into the internal branch 94 in a proximal direction toward the heart as shown in FIG. 8A. In FIG. 8B, a delivery sheath 76 follows over the guidewire 72. The delivery sheath 76 is pulled back in FIG. 8C to begin deployment of the small vessel stent graft 62 by revealing the fixation coupling 50. The fixation coupling 50 may be self-expanding or balloon expandable. The diameters of the fixation coupling 50 and the ring 55 are greater than the diameter of the internal branch 94, thus preventing the small vessel stent graft 62 from withdrawing from the internal branch 94 in a distal direction away from the internal branch opening 79. FIG. 8D shows the fixation coupling 50 fully deployed.

It is therefore intended that the foregoing detailed description be regarded as illustrative rather than limiting, and that it be understood that it is the following claims, including all equivalents, that are intended to define the spirit and scope of this invention.

The invention claimed is:

1. A branch vessel stent graft system comprising:
   a stent graft having a first open end, a second open end, a side wall, and a fenestration in the side wall, the fenestration having a diameter;
   a branch vessel stent graft having a proximal end, a distal end; a body portion configured for placement in a body vessel branching from a main body vessel, and a fixation coupling positioned at or near the proximal end and configured for placement within the fenestration;
   where the fixation coupling comprises a proximal end, a distal end, a distal non-helical ring coupled to the distal end and having a diameter, a proximal non-helical ring coupled to the proximal end and having a diameter, and a hyperboloid shaped region positioned between the non-helical rings and having an apex with a diameter, and first and second outer extents, where the diameters of both of the non-helical rings are larger than any diameter of the hyperboloid shaped region,
   where the diameter of the apex of the hyperboloid shaped region is greater than the diameter of the fenestration, and where, when the fixation coupling is placed within the fenestration the hyperboloid shaped region provides a fluid tight seal with the fenestration while permitting multi-directional movement of the branch vessel stent graft.

2. The branch vessel stent graft of claim 1 wherein the non-helical rings comprise radiopaque elements.

3. The branch vessel stent graft of claim 1 comprising any two or more of the following: distal and proximal non-helical rings having diameters larger than any diameter in the hyperboloid shaped region; elliptical distal or proximal non-helical rings; and elliptical distal or proximal non-helical rings having a directrix larger than any diameter in the hyperboloid shaped region.

4. A system for repairing an anatomical vessel at the junction of a main anatomical vessel and branch anatomical vessel comprising: a primary stent graft configured for placement in the main anatomical vessel, comprising a tubular graft material, at least one stent, a fenestration in a sidewall of the tubular graft material, the fenestration having a diameter; a branch vessel stent graft comprising: a proximal end, a distal end, a body portion configured for placement in the branch anatomical vessel branching from the main anatomical vessel; and a fixation coupling positioned at or near the proximal end and configured for placement within the fenestration; where the fixation coupling comprises a distal non-helical ring having a diameter, a proximal non-helical ring having a diameter, and a hyperboloid shape region positioned between the non-helical rings, and first and second outer extents, where the diameter of at least one of the non-helical rings is larger than any diameter of the hyperboloid shaped region; and where the smallest diameter of the hyperboloid shaped region is greater than the diameter of the fenestration,
  where, when the fixation coupling is placed within the fenestration the hyperboloid shaped region provides a fluid tight seal with the fenestration while permitting multi-directional movement of the branch vessel stent graft, and
  wherein the distal or proximal non-helical ring is a non-circular ellipse with a directrix.

5. The branch vessel stent graft of claim 4 wherein the directrix of the distal or proximal non-helical ring is greater than any diameter in the hyperboloid shaped region.

* * * * *